United States Patent [19]

Hutterer et al.

[11] Patent Number: 4,641,652
[45] Date of Patent: Feb. 10, 1987

[54] APPLICATOR FOR TYING SEWING THREADS

[75] Inventors: Frieder Hutterer, Cologne; Gerd Buess, Pulheim; Manfred Boebel, Oetisheim, all of Fed. Rep. of Germany

[73] Assignee: Richard Wolf GmbH, Fed. Rep. of Germany

[21] Appl. No.: 721,669

[22] Filed: Apr. 10, 1985

[30] Foreign Application Priority Data

Apr. 12, 1984 [DE] Fed. Rep. of Germany ....... 3413744

[51] Int. Cl.$^4$ .................. A61B 17/04; D05B 1/00; D05B 87/00; D03J 3/00
[52] U.S. Cl. .................. 128/334 R; 223/99; 289/17; 112/154
[58] Field of Search .................. 289/1.5, 2, 1.6, 17, 289/15, 18; 128/334 R, 335.5, 339, 340; 223/99; 112/154, 156, 160

[56] References Cited

U.S. PATENT DOCUMENTS

| 919,138 | 2/1909 | Drake et al. | 128/340 |
| 1,176,032 | 3/1916 | Cole | 128/339 |
| 3,840,017 | 10/1974 | Violante | 128/340 |
| 4,538,594 | 9/1985 | Boebel et al. | 128/6 |

FOREIGN PATENT DOCUMENTS 910796 2/1958 United Kingdom ............... 289/17

Primary Examiner—Richard C. Pinkham
Assistant Examiner—Gary Jackson
Attorney, Agent, or Firm—Hill, Van Santen, Steadman & Simpson

[57] ABSTRACT

The applicator for utilization in combination with an endoscope tube comprises a coil connected to a longitudinal passage through a shaft and comprising hollow turns connected to the shaft passage for reception of a sewing thread, whose proximal extremity is passed through a loop projecting from a radial opening at the distal extremity of the shaft, is then drawn through the shaft passage and fastened to the proximal shaft extremity. Tying the single stitch after piercing the tissues is performed by passing the needle axially through the coil and then around the thread and twisting the coil out of the loop formed thereby to form the first half of a knot which is then complemented by the second half of the knot tied in the same way, the knot being tied by subsequently pulling together the two said halves.

14 Claims, 16 Drawing Figures

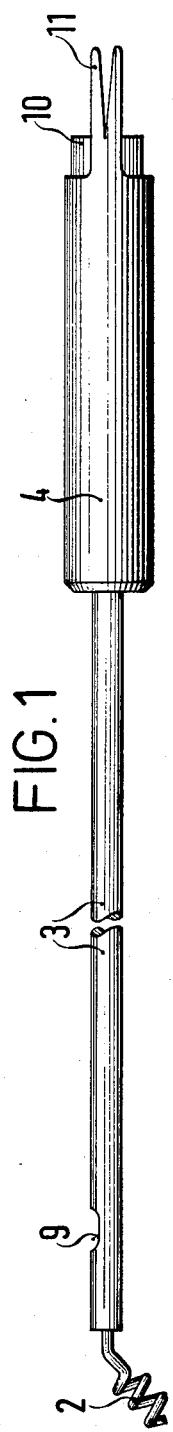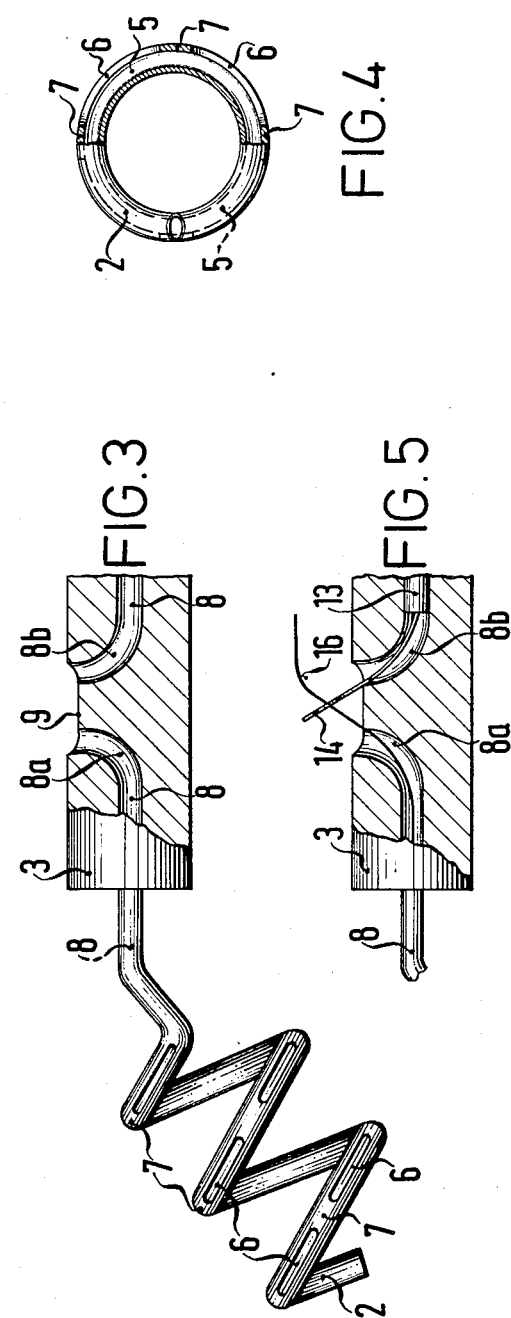

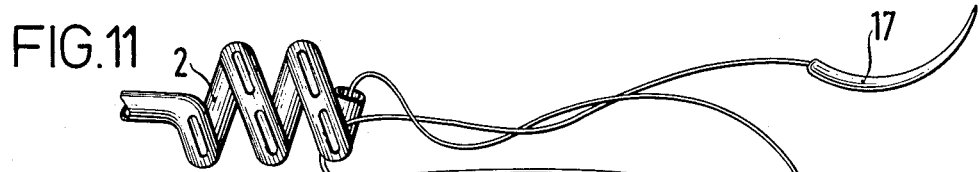
FIG.11
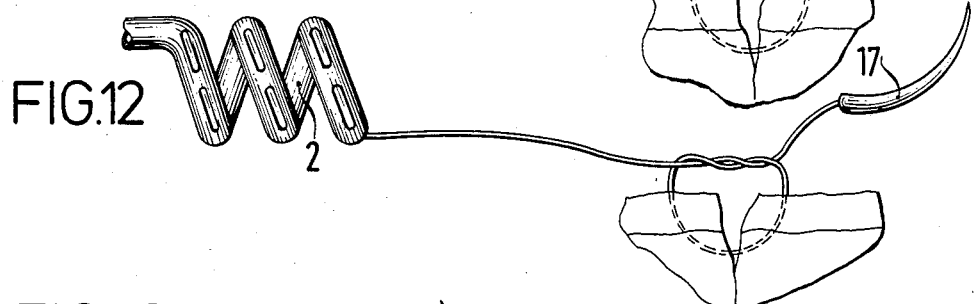
FIG.12
FIG.13
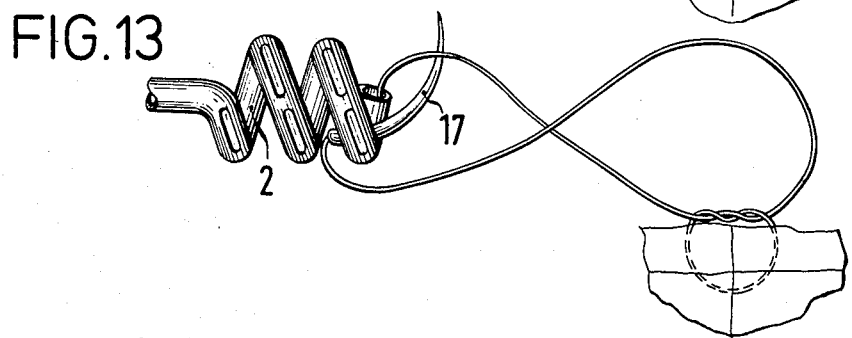
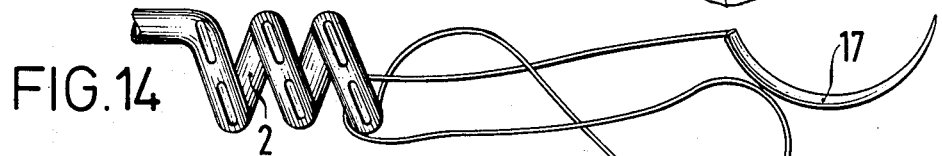
FIG.14
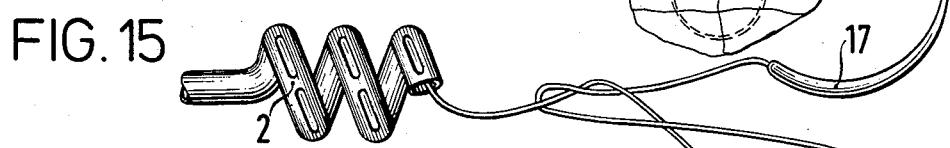
FIG.15
FIG.16
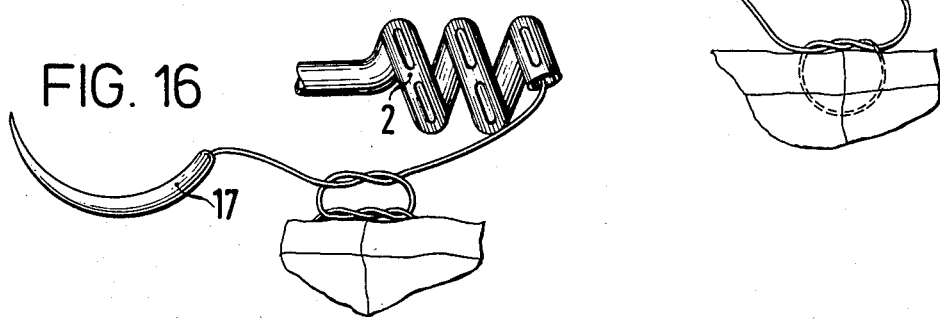

APPLICATOR FOR TYING SEWING THREADS

BACKGROUND OF THE INVENTION

1. Field of the Invention

The invention relates to an applicator for tying a thread for stitching a wound with individual stitches.

2. Description of the Prior Art

Different techniques are known for stitching wounds in bodily cavities by means of a thread which has to be tied. These however require difficult manipulations with needle and thread under considerable expenditure of patience and time and a specific routine.

SUMMARY OF THE INVENTION

The object of the invention consists in providing a device which may be handled in an uncomplicated manner and allows of reliable and rapid tying of threads for individual stitches in body cavities through a long endoscope tube.

In accordance with the invention, this problem is resolved in the case of the applicator defined in the foregoing by means of a coil comprising hollow windings for reception of a thread which coil is advantageously joined at an angle to an axial passage of a shaft. The thread passes through said axial passage and has an extremity led to the outside at a distal position of the applicator and may at this point be secured in an auxiliary device. Then the thread may be drawn through the shaft passage and immobilised at the proximal shaft extremity.

The applicator in accordance with the invention may be utilised with an endoscope tube, for example as shown in the German patent specification No. 3319049, so that the thread led through the coil and shaft may be offered up together with the needle to the wound which is to be stitched, to which end the wound walls are pierced by the needle using a needle holder which is also led through the endoscope tube, both under observation.

Drawing a thread provided with a needle into the applicator is performed prior to the insertion of the applicator through the endoscope tube into the bodily cavity space, as will be described in the following with reference to the drawings in which an example is illustrated.

BRIEF DESCRIPTION OF THE DRAWINGS

FIG. 1 is a side view of the applicator in accordance with the invention,

FIG. 2 is a side view of an auxiliary device for drawing the thread through the applicator shaft, FIG. 3 is an enlarged side view of a distal extremity of the applicator with portions broken away, FIG. 4 is an end view with portions broken away of the applicator winding, FIG. 5 is an enlarged side view with a portion broken away of the distal shaft extremity with the sewing thread end and loop of the auxiliary device according to FIG. 2, FIGS. 13 to 15 are partial side views that show the stages for forming the second half of a knot, FIG. 16 is a partial side view that shows the closing of the double knot.

DETAILED DESCRIPTION OF THE PREFERRED EMBODIMENTS

Figure 6:
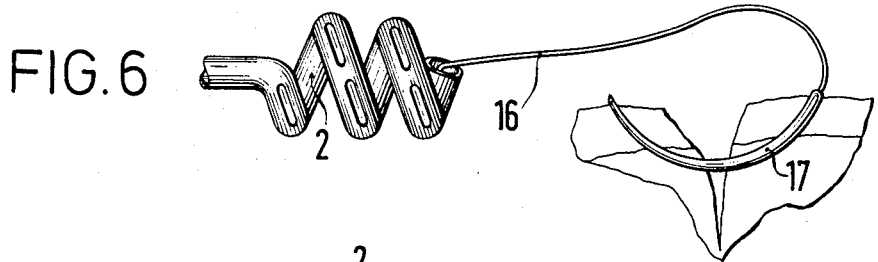
FIG. 6 is a partial side view that shows the application of a single stitch, with a reduced number of windings of the coil as compared to FIG. 3, FIGS. 7 to 12 are partial side views that show the stages for forming the first half of a knot.

The applicator 1 comprises a helical tubular coil 2 having at least one full turn, which is advantageously connected to the distal shaft extremity at an angle to a shaft 3, which has a handle 4. The hollow turns of the coil form a passage 5 whose wall is slotted at the outside along part lengths of the turns, so that these slots 6 are delimited at their extremities by residual wall portions 7.

The coil passage 5 is followed by a short distal length of a longitudinal duct through the shaft in the form of an axial shaft passage 8 which has a bend 8a led radially outwards and then has a bend 8b led back to the proximal length of the axial shaft passage 8. Between the arcuate passage sections 8a and 8b, the shaft wall is transversely connected to an excision 9 in the form of a longitudinal channel in the outer surface of the shaft 3.

The shaft passage 8 may be closed off proximally by means of an elastic seal 10 against the atmosphere, and the handle is extended proximally by two mutually opposed handle sections 11 which advantageously have a V-shaped incision for gripping a sewing thread end.

An auxiliary device 12 according to FIG. 2, whose function will also be described, is provided moreover for utilisation with the applicator 1. The auxiliary device comprises a rod 13 which has an elastic catcher loop 14 (wire eye). A sleeve 15 providing a stop is pushed over the distal extermity of the rod 13 and inserted together with the same through the seal 10 into the passage 8 of the shaft 3, until the stop 15a bears on the seal. The rod 13 may then be passed through the passage 8 without damaging the loop 14, until the elastic loop 14 projects outwards via the deflector section 8a (FIG. 5).

The applicator is utilised in the following manner to form a double-loop knot for a sewing thread.

Figure 7:
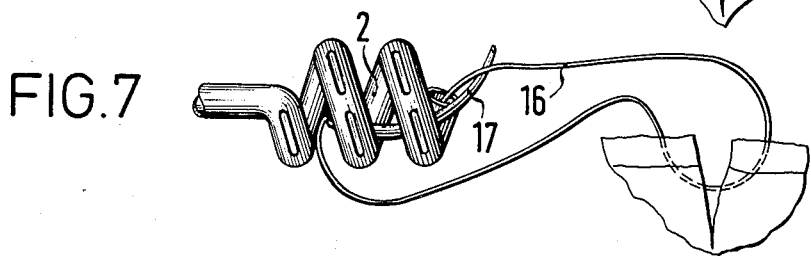
Figure 8:
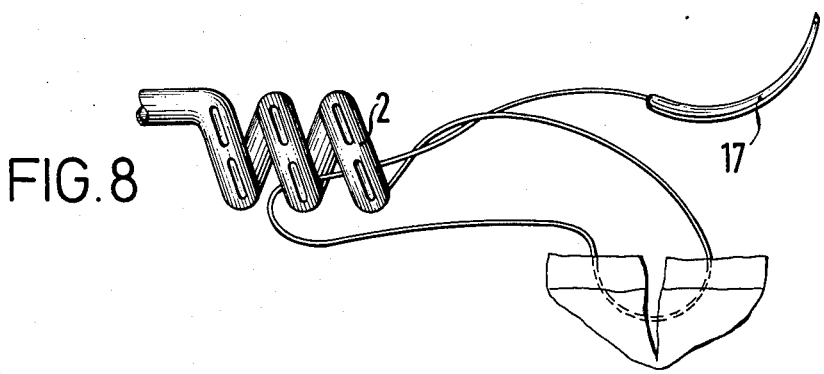
Figure 9:
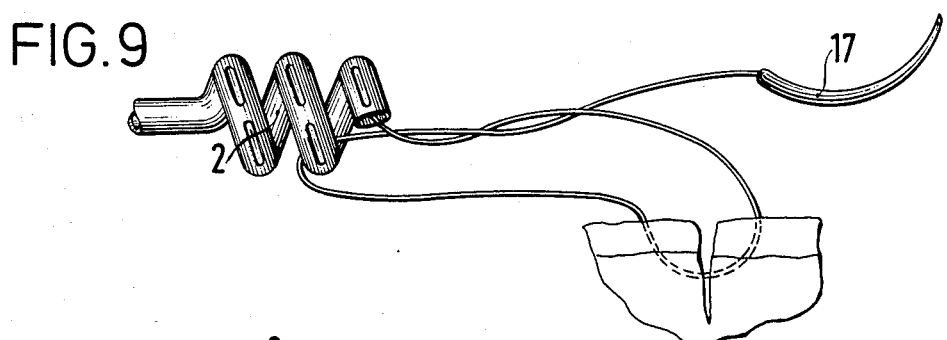
Figure 10:
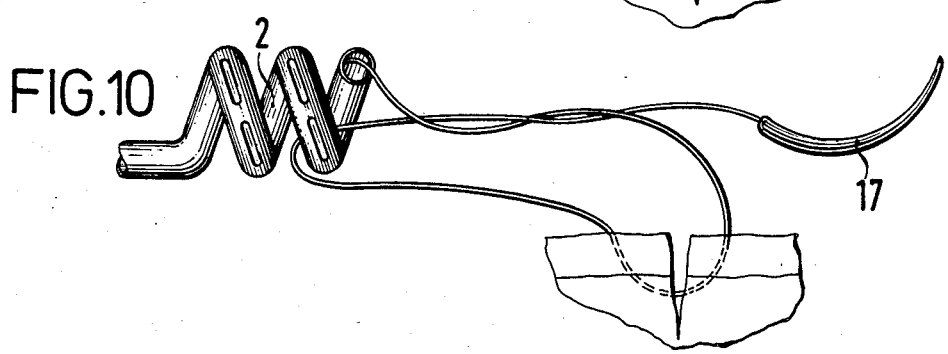

A sewing thread 16 is inserted manually into the distal extremity of the coil passage 5 and pushed through the coil 2, to which end thinner threads passing to the outside via the slots 6 may in each case be pushed back into the passage 5 under the residual wall sections 7. According to FIG. 5, the thread 16 will finally emerge from the excision 9 via the deflector section 8a and be passed through the loop 14. The thread is drawn along by drawing the rod 13 back with the thread 16 within the loop 14, until it projects out of the proximal extremity of the shaft 3, so that it may be led in a figure-8 around the securing means 11 and gripped in an incision 11. The protective sleeve 15 is also removed together with the rod 13. The applicator 1 carrying the sewing thread which is distally provided with a needle in conventional manner may now be introduced into the body cavity through an endoscope tube, e.g. according to German patent application No. 3319049. The needle 17 may then be gripped by means of a needle holder which is also inserted into the body cavity via the tube, and the single stitch may be made according to FIG. 6. The needle 17 is then pulled axially through the coil 2 (FIGS. 7 and 8) and laid around the thread end projecting out of the coil 2. The coil 2 is then twisted out of the loop formed thereby, by turning the applicator 1, so that the thread 16 forms the first half of a knot (FIG. 8). The thread loop is then pulled together according to FIG. 12, that is to say by holding the needle 17 fast and pulling the applicator whereof the proximal handle extremity has the thread fastened to it.

The needle 17 is then pulled through the coil 2 again axially by means of the needle holder according to FIG. 13, and the coil 2 is twisted out of the loop (FIG. 14) so that the second half of a knot is formed thereby which, as apparent from FIGS. 15 and 16, ties the knot upon being pulled tight.

After this, the two thread ends may be cut off, the needle and the applicator may be withdrawn from the body cavity and the applicator may be prepared for the next individual stitch.

What is claimed is:

1. An applicator for tying threads for stitching wounds with single stitches comprising:
    a shaft with proximal and distal ends having a longitudinal duct therethrough for a thread, said shaft having a radial opening adjacent the distal end to provide access to said duct;
    means at the proximal end of said shaft for securing a thread passing through said duct;
    a hollow open-ended helical tube extending from the distal end of said shaft with an inside of said tube communicating with a distal portion of said duct to enable said thread to pass through said helical tube, and
    an auxiliary device in the form of a rod insertable through said duct in said shaft, said rod having a flexible loop at one end thereof for attachment to a thread to enable said thread to be drawn through said duct from said radial opening to said securing means at the proximal end of said shaft.

2. An applicator according to claim 1, wherein said helical tube extends at an oblique angle relative to said shaft.

3. An applicator according to claim 1, further comprising a handle at the proximal end of said shaft.

4. An applicator according to claim 3, wherein said securing means comprises a pair of resilient projections extending on the handle, said projection being adapted to grip a thread between them.

5. An applicator according to claim 1, wherein slots are provided in a wall of said helical tube.

6. An applicator according to claim 1, wherein said duct is divided adjacent said radial opening into proximal and distal portion with each portion turning radially outward to said opening.

7. An applicator according to claim 6, wherein said radial opening is in the form of a channel formed in a wall of said shaft and connecting the respective radially outwardly turned portions of said proximal and distal portions of said duct.

8. An applicator for tying threads for stitching wounds with single stitches comprising:
    an elongate shaft having proximal and distal ends;
    a hollow helical tube attached to the distal end of the shaft, said tube being coiled around a central axis which extends at an oblique angle to said shaft, and having elongate slots therein spaced at intervals along its windings;
    a first axial duct portion within said shaft, communicating at its distal end with an inside of said helical tube and at its proximal end turning radially outwardly and opening into a longitudinal channel formed in the outer surface of said shaft towards the distal end thereof;
    a second axial duct portion within said shaft, extending from the proximal end of the shaft to said longitudinal channel and turning radially outwardly at its distal end to open into said channel;
    a handle at the proximal end of said shaft;
    a pair of resilient projections extending rearwardly from said handle and defining between them a slot for retention of a thread extending through said first and second duct portions and said helical tube and
    an auxiliary device for drawing a thread through said second duct portion from said longitudinal channel to the proximal end of said shaft, said auxiliary device comprising a rod dimensioned to be inserted into said second duct portion and having at one end thereof a wire loop for attachment of said thread.

9. An applicator for tying threads for stitching wounds with single stitches comprising:
    a shaft with proximal and distal ends having a longitudinal duct therethrough for a thread, said shaft having a radial opening adjacent its distal end to provide access to said duct, said duct being divided adjacent said radial opening into proximal and distal portions with each portion turning radially outward to said opening;
    means at the proximal end of said shaft for securing a thread passing through said duct and
    a hollow open-ended helical tube extending from the distal end of said shaft, the inside of said tube communicating with a distal portion of said duct to enable said thread to pass through said helical tube.

10. An applicator according to claim 9, wherein said radial opening is in the form of a channel formed in a wall of said shaft and connecting the respective radially outwardly turned portions of said proximal and distal portions of said duct.

11. An applicator according to claim 10, wherein said helical tube extends at an oblique angle relative to said shaft.

12. An applicator according to claim 10, wherein slots are provided in the walls of said helical tube.

13. An applicator according to claim 10, further including a handle at the proximal end of said shaft.

14. An applicator according to claim 13, wherein said thread securing means comprises a pair of resilient projections on said handle adapted to grip a thread between them.

* * * * *